United States Patent [19]

Tokarz et al.

[11] Patent Number: 4,681,572

[45] Date of Patent: Jul. 21, 1987

[54] FEMALE URINARY INCONTINENCE DEVICE

[75] Inventors: Joseph S. Tokarz, Schaumburg; Marvin E. Jensen, Niles, both of Ill.

[73] Assignee: Hollister Incorporated, Libertyville, Ill.

[21] Appl. No.: 516,931

[22] Filed: Jul. 27, 1983

Related U.S. Application Data

[63] Continuation-in-part of Ser. No. 417,140, Sep. 13, 1982, abandoned.

[51] Int. Cl.[4] .............................................. A61F 5/44
[52] U.S. Cl. .................................... 604/329; 128/761; 128/774
[58] Field of Search ............... 128/760, 761, DIG. 21, 128/774, 775, 778; 604/327–329, 330, 331, 347, 353, 354, 349, 350, 119, 129; 4/144.1–144.4; 137/588, 854

[56] References Cited

U.S. PATENT DOCUMENTS

| | | | |
|---|---|---|---|
| 2,483,079 | 9/1949 | Williams | 128/295 |
| 2,490,969 | 12/1949 | Kinyon | 4/110 |
| 2,786,467 | 3/1957 | Price | 137/588 |
| 3,116,734 | 1/1964 | Terman | 128/295 |
| 3,194,238 | 7/1965 | Breece | 604/329 |
| 3,512,185 | 5/1970 | Ellis | 4/110 |
| 3,528,423 | 9/1970 | Lee | 604/329 |
| 3,629,873 | 12/1971 | Long | 4/144.2 |
| 3,651,810 | 3/1972 | Ormerod | 128/295 |
| 3,661,155 | 5/1972 | Lindan | 128/295 |
| 3,683,894 | 8/1972 | Villari | 128/767 |
| 3,776,235 | 12/1973 | Ratcliffe | 128/295 |
| 3,995,329 | 12/1976 | Williams | 604/329 |
| 4,160,383 | 7/1979 | Rauschenberger | 604/129 |
| 4,194,508 | 3/1980 | Anderson | 604/329 |
| 4,198,979 | 4/1980 | Cooney | 128/295 |
| 4,246,901 | 1/1981 | Frosch | 128/761 |
| 4,270,539 | 6/1981 | Frosch | 604/347 |
| 4,421,511 | 12/1983 | Steer | 604/329 |
| 4,496,355 | 1/1985 | Hall et al. | 604/327 |

FOREIGN PATENT DOCUMENTS

| | | |
|---|---|---|
| 2300545 | 6/1976 | France . |
| 1059680 | 9/1967 | United Kingdom . |
| 1467144 | 7/1977 | United Kingdom . |
| 2015347 | 9/1979 | United Kingdom . |
| 2072512 | 10/1981 | United Kingdom . |
| 2090144 | 7/1982 | United Kingdom . |

OTHER PUBLICATIONS

Dow Corning, Q7-4290 Prosthetic Foam, Dow Corning Corp., Midland, Mich. 48640, Jan. 1979.
New Product Information, Silastic ® Q7-4840 A/B Medical Grade Liquid Silicone Rubber, Dow Corning Corp. (Published 1981).

Primary Examiner—C. Fred Rosenbaum
Assistant Examiner—J. L. Kruter
Attorney, Agent, or Firm—Tilton, Fallon, Lungmus

[57] ABSTRACT

A female urinary incontinence device including a periurethral cup, an external pad, and an elastic tubular bellows extending therebetween, as well as associated elements for holding the device in place and for collecting urine flowing therethrough. The periurethral cup is molded in one piece soft compressible material and has walls of substantial thickness providing smoothly rounded surfaces for sealingly contacting surfaces of the periurethral floor and vaginal introitus. One wall portion of the cup curves upwardly to define a resilient urine-deflecting protuberance received within the vaginal introitus. The device also includes a conduit for directing urine to a collector, a valved port for allowing air to enter the system within the external pad to prevent the development of relative negative pressure within that system, and a vent for allowing gas to escape from the collector.

18 Claims, 16 Drawing Figures

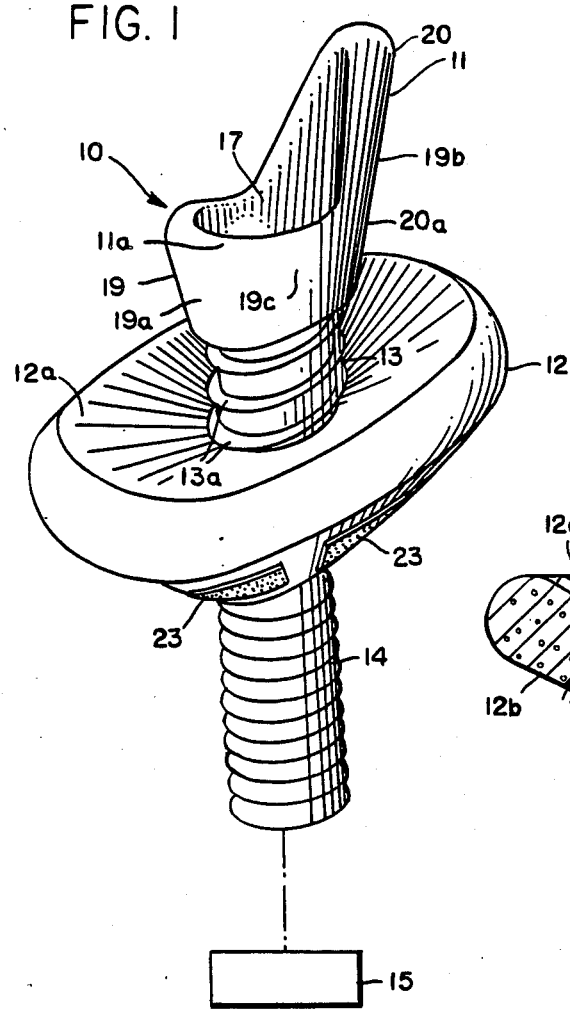
FIG. 1
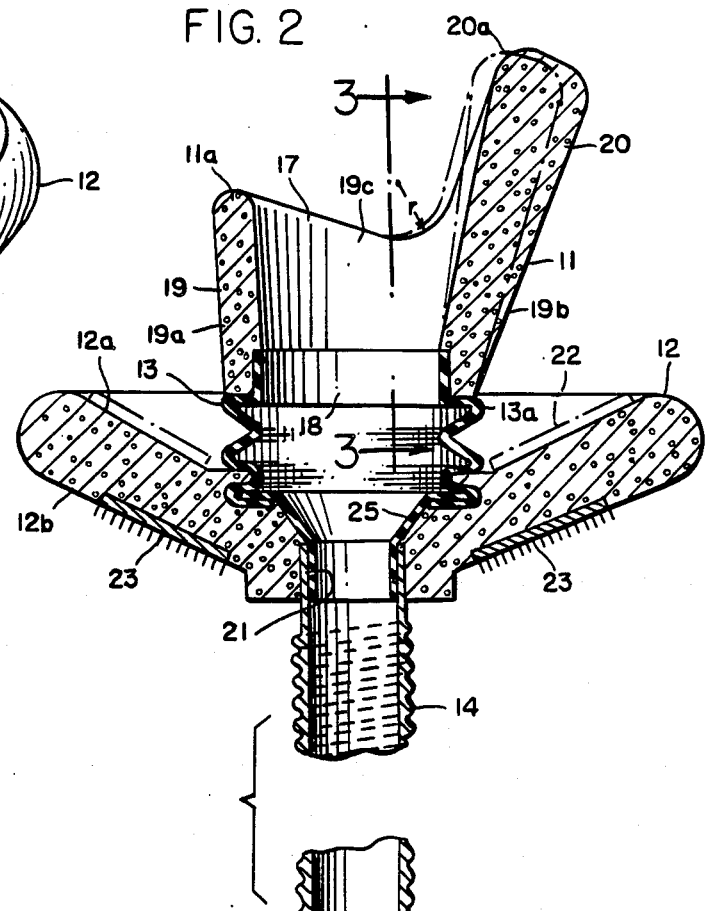
FIG. 2
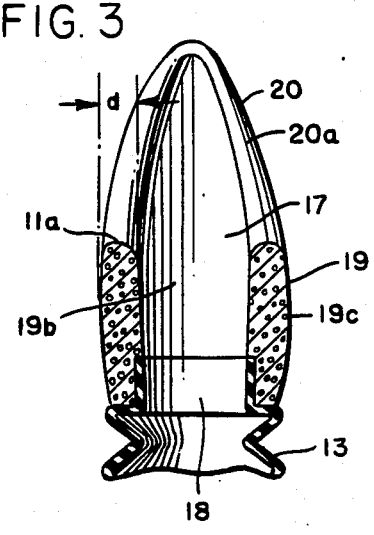
FIG. 3
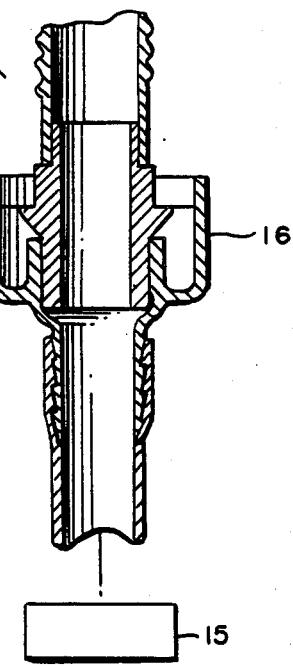

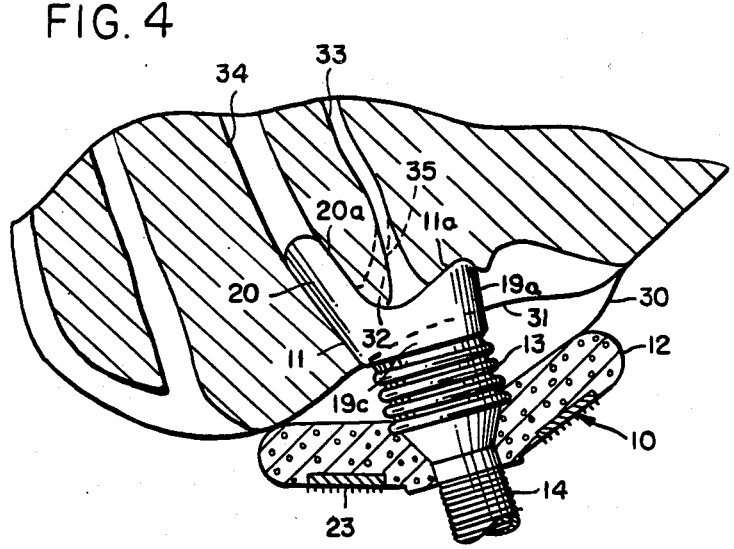
FIG. 4
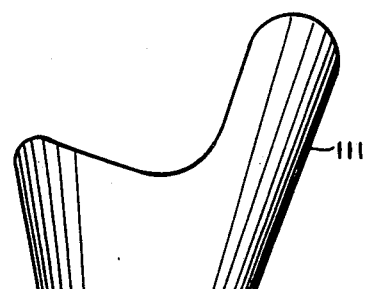
FIG. 7
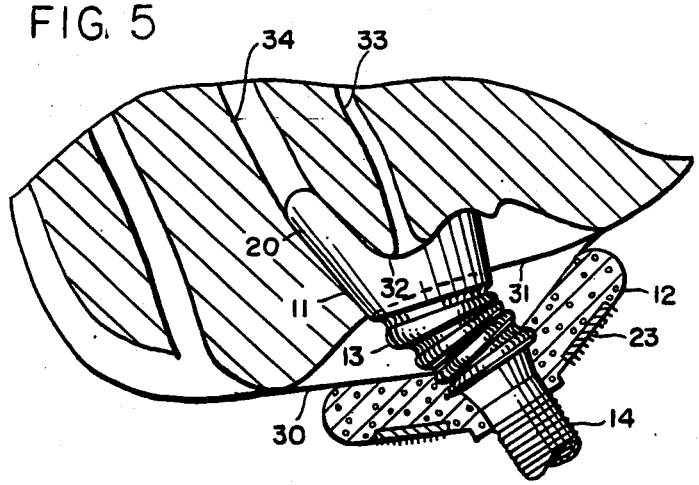
FIG. 5
FIG. 6
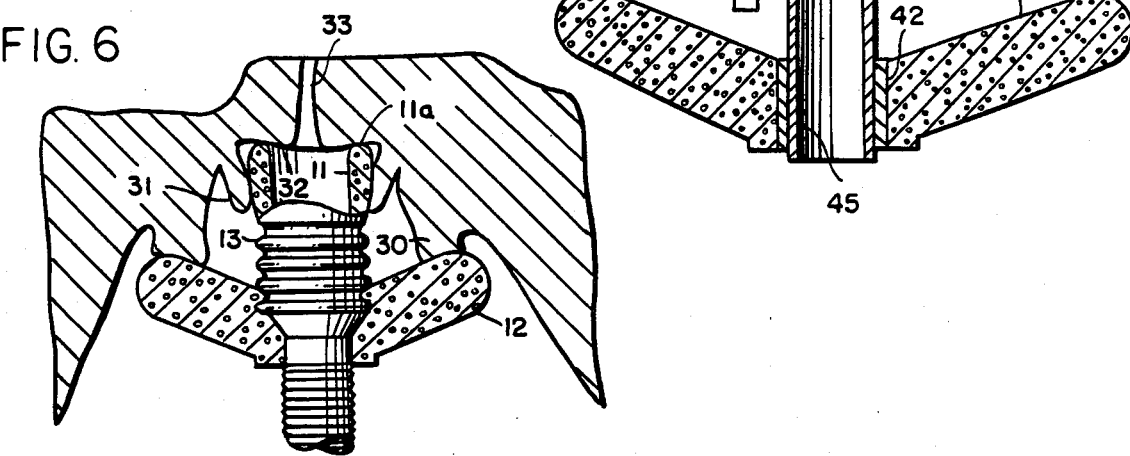

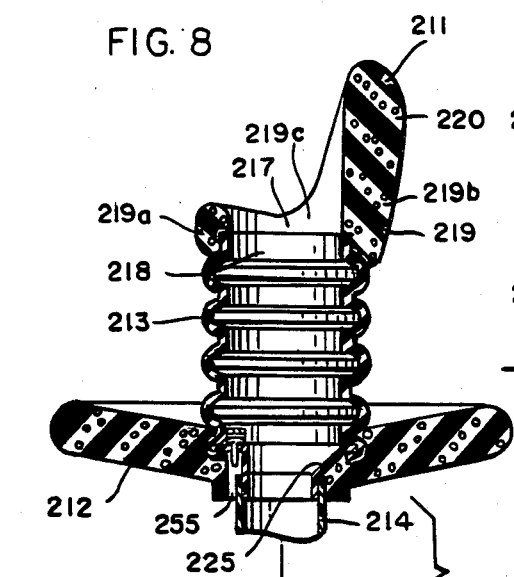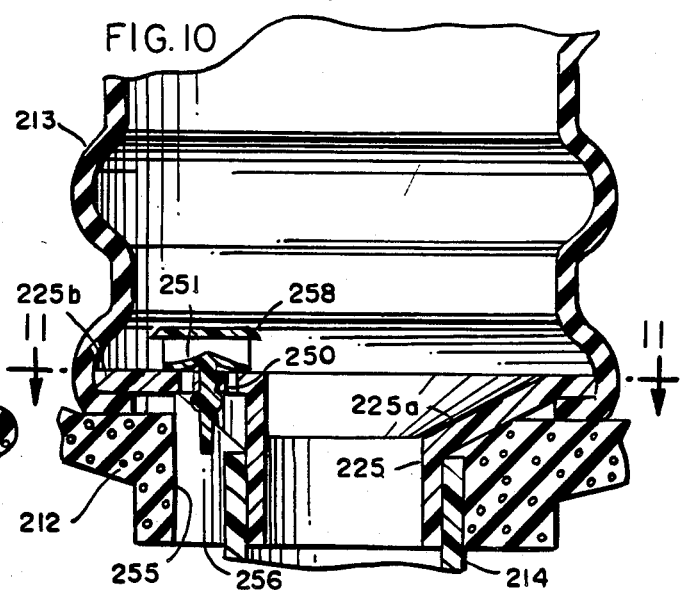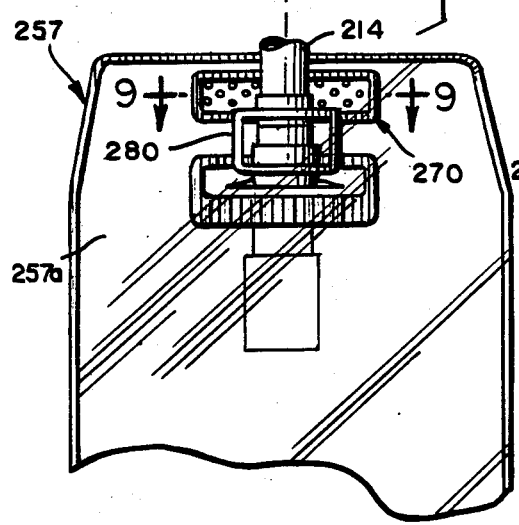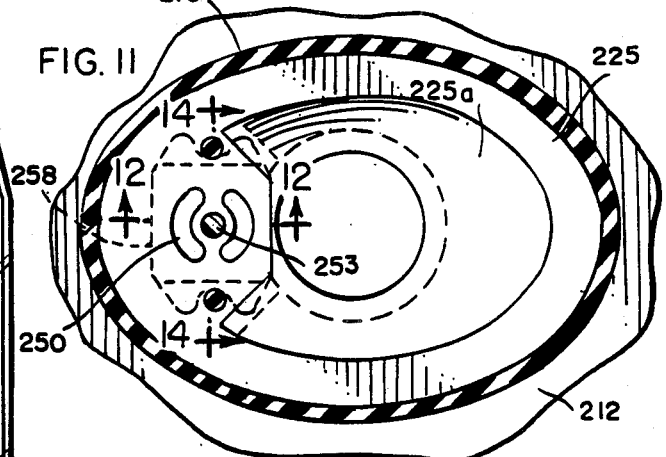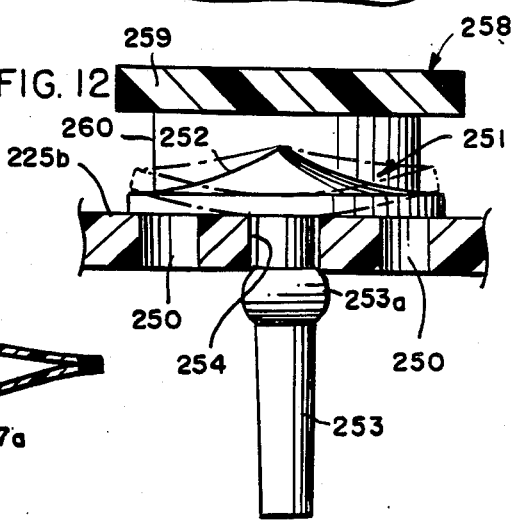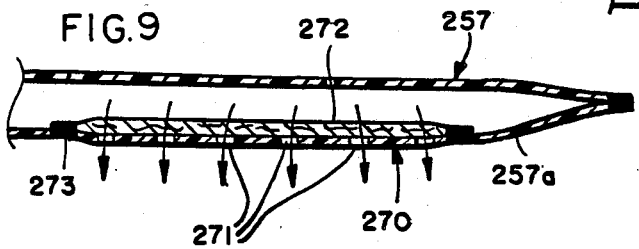

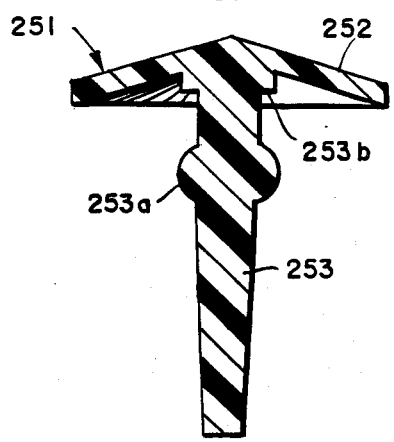
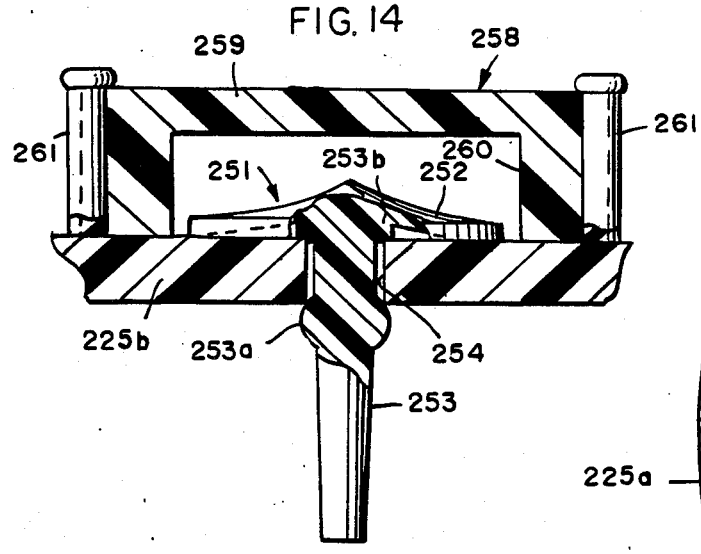
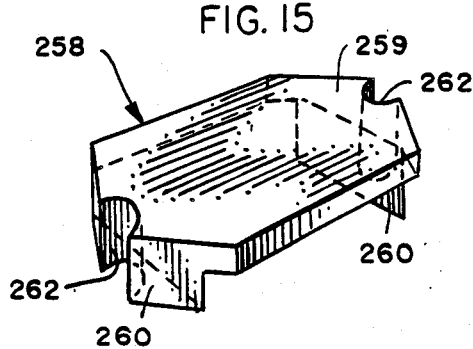
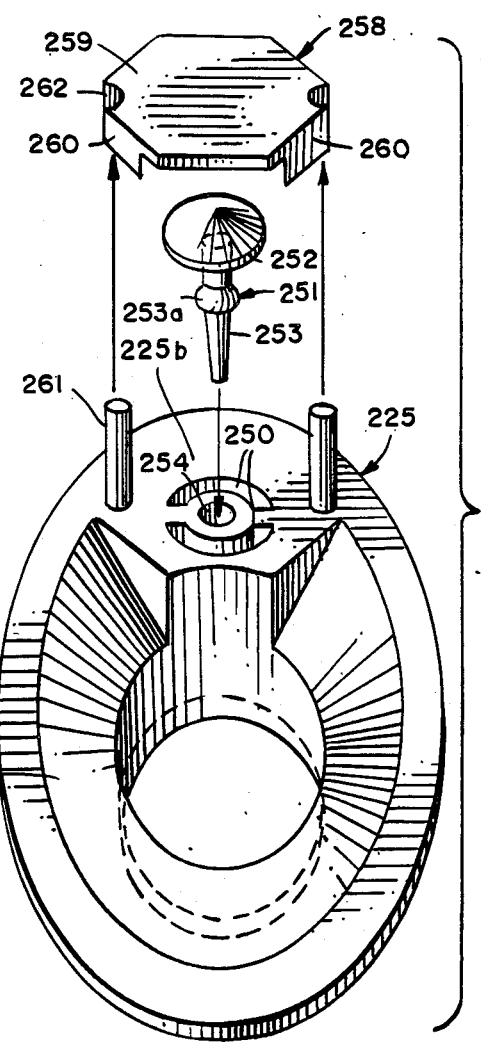

FEMALE URINARY INCONTINENCE DEVICE

RELATED APPLICATION

This application is a continuation-in-part of our co-pending application Ser. No. 417,140, filed Sept. 13, 1982 now abandoned.

BACKGROUND

Various devices have been proposed in past years for directing and collecting urine from female patients suffering from urinary incontinence but, in general, such devices have been associated with problems of leakage, wearer discomfort, pressure sores, and even necrosis. An indication of the ineffectiveness of such prior devices lies in their lack of commercial success.

The problems associated with prior devices are particularly pronounced with ambulatory patients because of the varied and complex anatomical changes that occur in the periurethral area during locomotion and the failure of such devices to coapt to such changes. However, the need for an effective device is by no means limited to ambulatory patients. For example, non-ambulatory female patients with spinal cord injuries are not served well by existing devices (indwelling catheters, intermittent catheters, diapers, etc.) despite only minimal body movement of such patients.

Prior patents have disclosed female urinary collection devices equipped with locating elements intended to be inserted into the vagina for retaining the collection devices in operative positions. Reference may be had to U.S. Pat. Nos. 2,483,079, 2,490,969, 3,116,734, 3,528,423, 3,512,185, 3,776,235, 3,661,155, and 4,246,901. Those constructions in which the locating elements are relatively rigid clearly fail to conform with the anatomical changes occurring during body movement. While prior devices with flexible or deformable vaginal locating elements may reduce tissue irritation and increase patient comfort, problems in providing an effective seal and avoiding leakage along the lines or zones of contact have nevertheless remained.

Other patents of interest are U.S. Pat. Nos. 4,270,539, 3,651,810, 4,198,979, and 3,194,238.

SUMMARY

One aspect of this invention lies in the discovery that effective sealing engagement with perimeatal tissues may be achieved if the female incontinence device is constructed so that the periurethral cup is compressible but generally form-retaining and is mounted so that it may move independently, at least to a limited extent, with respect to those portions of the device that make external contact with the wearer. A further aspect lies in the recognition that if such a molded compressible element is cup-shaped in configuration and is operatively connected to an external pad (which is in turn held in place by a panty or supporting belts) by means of a tubular elastic bellows that exerts an upward force on the cup when the device is worn without, at the same time, interfering with limited independent movement of the cup with respect to the pad, such a combination will result in a device that eliminates or substantially reduces the aforementioned problems associated with prior devices. An air entry port, normally closed by a one-way valve, allows air to enter the system to prevent the development of relative negative pressure within that system, and a vent is provided in the collector to prevent expansion or deformation of the collector (normally an expandable plastic pouch) that might otherwise result from entrapped air and the development of a relative positive pressure.

The periurethral cup of a device embodying this invention is molded in one piece of soft, compressible but generally form-retaining material having a durometer within the range of about 1 to 30 on the Shore A scale, the preferred range being approximately 5 to 20 on that scale. An elastomeric material, molded so that the outer surfaces of the cup are smooth and non-porous, has been found particularly effective.

The periurethral cup is provided with front, rear, and lateral wall portions defining upper and lower openings, such wall portions having a substantial wall thickness (about 3 to 15 millimeters) and having smoothly rounded surfaces, for making substantial surface contact with the periurethral floor and vaginal introitus. The rear wall portion extends upwardly beyond the upper limits of the front and lateral portions to define a resilient, vaginally-insertable, urine-deflecting protuberance, a feature of importance for those patients whose urethral orifice is located in, or immediately adjacent to, the vaginal introitus. The urine-deflecting protuberance is capable of flexing towards and away from the entrance opening of the cup without causing buckling or kinking of the smoothly-rounded contact surfaces engaging the periurethral floor and vaginal introitus because of the compressibility and substantial wall thickness of the cup.

An external pad of soft, resilient and flexible material is dimensioned for externally contacting the labia majora of the wearer and has an opening extending therethrough. Between that opening and the lower opening of the periurethral cup is a tubular elastic bellows dimensioned for exerting an upward force on the cup, when the device is worn, to maintain an effective seal between the rounded contact surfaces of the cup and the surfaces of the periurethral floor and introitus despite the complex anatomical changes or displacements that occur during the dynamics of body movement. The length of the elastic bellows varies within certain predetermined limits according to the distance between the periurethral floor and the external surfaces of the labia majora for each wearer, and a sizing instrument, patterned after the construction of the urinary incontinence device, may be used to establish the proper bellows length for a given patient. Such sizing tool designed to allow endoscopic examination if deemed necessary or desirable.

The external pad may, if desired, be provided with a soft absorbent liner for directly contacting the labia majora of the patient. Flexible tubing extends from the outlet of the external pad to a leg bag or other suitable collection device. The external pad is preferably held in place by the wearer's undergarment (panty), but other supporting means in the form of straps or belts may be used.

Other features, advantages, and objects of the invention will become apparent from the drawings and specification.

DRAWINGS

FIG. 1 is a perspective view of a female urinary incontinence device embodying the invention.

FIG. 2 is a vertical longitudinal sectional view of the device.

FIG. 3 is an enlarged cross sectional view taken along line 3—3 of FIG. 2.

FIG. 4 is a saggital sectional view illustrating the device as it is worn.

FIG. 5 is a saggital sectional view similar to FIG. 4 but illustrating the relative displacements of the external pad and periurethral cup during wearer movement.

FIG. 6 is a lateral sectional view of the device as it is worn.

FIG. 7 is a side elevational view, shown partly in section, of a sizing tool adapted to be used as part of the present invention.

FIG. 8 is a fragmentary side view, taken partly in section, showing a modified device with ports or vents for preventing collapse of the bellows and conduit while at the same time allowing gas to escape from the pouch.

FIG. 9 is an enlarged horizontal cross sectional view of the pouch's vent and filter, with certain elements of the pouch and associated coupling omitted for clarity of illustration.

FIG. 10 is an enlarged vertical sectional view of certain portions of the device depicted in FIG. 8.

FIG. 11 is a horizontal sectional view taken along line 11—11 of FIG. 10.

FIG. 12 is a still further enlarged sectional view of the inlet port and valve member taken along line 12—12 of FIG. 11.

FIG. 13 is a sectional view of the umbrella valve member showing details of construction thereof.

FIG. 14 is an enlarged sectional view taken along line 14—14 of FIG. 11.

FIG. 15 is a perspective view of a fluid-deflecting element.

FIG. 16 is an exploded perspective view of the valve member, fluid deflector, and the portion of the device providing the valve passage or port.

DETAILED DESCRIPTION OF PREFERRED EMBODIMENT

Referring to the embodiment shown in FIGS. 1-6, the primary components of the female urinary incontinence device 10 are periurethral cup 11, external pad 12, and tubular elastic bellows 13. A flexible tube 14 carries urine to a suitable collector or receptacle 15. For an ambulatory patient, collector 15 would ordinarily take the form of a leg bag, such as the bag disclosed in co-owned application Ser. No. 273,363, filed June 15, 1981. It is to be understood, however, that other types of collectors might be provided to suit the needs and physical condition of the user. Ordinarily, flexible tube 14 would include a suitable detachable coupling 16. The coupling illustrated in FIG. 2 is similar to that shown and described in U.S. Pat. No. 4,280,498, but other types of couplings may be provided.

The periurethral cup 11 is molded in one piece from a soft, compressible, but generally form-retaining material. A molded elastomeric silicone material having a smooth, substantially non-porous outer surface has been found particularly effective, but other molded compressible materials, such as elastomeric foam materials, might be used. Regardless of the material selected, it is believed critical that such material should have a durometer within the range of about 1 to 30 on the Shore A scale, preferably within the range of 5 to 20. Particularly effective results have been obtained with a material having a durometer of approximately 10.

It is also important that the side wall of the periurethral cup have substantial thickness and that the uppermost surfaces of the cup be smoothly curved or rounded as shown most clearly in FIGS. 2 and 3. More specifically, as depicted in the drawings, the cup has upper and lower openings 17 and 18, respectively. The integral side wall 19 is composed of front, rear, and lateral wall portions 19a, 19b, and 19c, respectively. In the region bordering top opening 17, each of those wall portions should have a thickness d (FIG. 3) within the range of about 3 to 15 millimeters. The result is a cup which, as brought out hereinafter, has upper surfaces making substantial contact with the periurethral floor and vaginal introitus and which, although soft and compressible, tends to be shaperetentive in use notwithstanding the upward force exerted by elastic bellows 13.

The rear wall portion 19b curves upwardly beyond the upper limits of the front and lateral wall portions to define a resilient, vaginally-insertable, urine-deflecting extension or protuberance 20. The essential purpose of the protuberance is to serve as a urine deflector for that portion of the female population, estimated at between 15 to 20%, whose urethral orifice is located within, or immediatley adjacent to, the vaginal introitus. Any functions the protuberance performs in locating and retaining the cup in position are of secondary significance. As described more fully hereinafter, the wide-smoothly rounded contact surfaces of the compressible cup, in combination with the gentle upward force exerted by elastic bellows 13, serve primarily to maintain the cup in its operative position.

As shown in FIGS. 1-3, the rounded upper surfaces 20a of protuberance 20 merge smoothly and gradually with the upper surfaces 11a of the remaining side and front wall portions of the cup. Specifically, the upper front surfaces of the protuberance 20 merge with the upper surfaces of the side walls along a curved line represented in FIG. 2 as having a substantial radius r. That radius would normally fall within the range of about 5 to 12 millimeters. Of particular significance is the fact that even when the protuberance is urged forwardly, as indicated by broken lines in FIG. 2, no buckling or kinking of the wall occurs at radius r because of the compressibility of the material from which the cup is formed. Consequently, an effective seal between the curved upper surfaces of the cup (including the protuberance) and the contact surfaces of the patient tends to be maintained during normal body movement.

External pad 12 may be formed of the same soft, compressible material as periurethral cup 11 and, in any event, should be formed of a resilient, flexible polymeric material. The pad is generally oval in outline, substantially larger than cup 11, and has a passage or opening 21 extending therethrough (FIG. 2). As shown in the drawings, the external pad has an upper surface 12a that is preferably concave or dish-shaped and, if desired, the upper surface may support an annular absorbent liner 22 (FIG. 2) formed of non-woven cotton fibers or other suitable absorbent material. Along its lower or external surface 12b, pad 12 may be provided with attachment means 23 in the form of fabric having nylon hooks or loops of the type commercially available under the Velcro designation. If such retaining means is used, then the patient would also wear a panty having a brushed nylon crotch panel for engaging and interlocking with attachment means 23, thereby helping to maintain the external pad 12 against the outer surfaces of the labia majora.

Bellows 13 may be formed of any suitable elastomeric material and, in an uncompressed or extended state, assumes the appearance depicted in FIGS. 1–3. The number of corrugations or convolutions 13a of the bellows for any given urinary collection appliance will depend on the distance between the labia majora and the periurethral floor of the wearer to be fitted with the device so that, when worn, the corrugations will be compressed or axially reduced as indicated in FIGS. 4 and 6. Ordinarily, for adult wearers, the number of corrugations will range between 2 (FIG. 2) to 6, and the undeformed length of the corrugated portion will range from 10 to 50 millimeters, with 3 selected sizes within those ranges meeting the requirements for over 90% of the adult female population. The tubular bellows may be formed of elastomers of polyurethane, silicone rubber, latex, or any of a variety of other materials having similar properties. A particularly effective material has been found to be a silicone rubber marketed by Dow Corning, Midland, Mich., under the designation Q7-4840; another, available from the same source, is MDX4-4210. Dow Corning literature identifies U.S. Pat. Nos. 3,445,420 and 4,162,243 as descriptive of Q7-4840 composition.

In the embodiment shown, the bellows 13 and cup 11 are formed separately and the upper end of the bellows is then secured by adhesive or by any other suitable means to the cup about the lower opening 18; however, it is to be understood that, if desired, the two elements may be formed integrally. The lower end of the bellows is connected to flexible tube or conduit 14 at the upper end of opening 21 of the external pad by means of an upwardly-flared extension 25 of conduit 14. Extension 25 of conduit 14 may be joined to the bellows 13, and to the wall of external pad 12, by adhesives, heat sealing, or any other suitable means.

FIGS. 4–6 depict the anatomical orientation of the urinary incontinence device 10 under normal conditions of use. External pad 12 bears upwardly against the external surfaces of the labia majora 30 and is held in that position by a panty or other support means (not shown) extending beneath the external pad and interlocked with the annular Velcro patch 23 (if provided). The periurethral cup 11 extends upwardly between the labia minora 31, and its soft rounded upper surfaces 11a of front and side wall portions 19a and 19c engage the periurethral floor 32 about the meatus of the urethra 33. The urine-deflecting protuberance 20 extends upwardly a short distance into the introitus of vagina 34. The gently-rounded upper surfaces 20a and 11a of the periurethral cup therefore make resilient sealing contact with the periurethral meatal surfaces even in the minority of cases where the patient's urethra curves rearwardly and communicates directly with the introitus (as represented in broken lines 35 in FIG. 4). The wide smoothly-rounded upper surfaces of the cup make substantial surface contact with the wearer and greatly reduce the possibility of localizing of forces that might result in discomfort and pressure necrosis. The thickness of the cup's walls yield a form-retaining construction despite the softness and compressibility of the material from which the cup is formed. Should limited deformation of the cup occur in use (as indicated, for example, by broken lines in FIG. 2), such deformation can be accommodated by the compressibility of the material of the cup without accompanying buckling or kinking actions that might result in leakage, and without relative movement between body tissues and the cup surfaces that might produce irritation and discomfort.

It is to be emphasized that the form-retentive cup is urged upwardly into sealing contact with the periurethral floor and introitus because of the expansive force exerted by elastomeric bellows 13. When the urinary incontinence device is properly worn, the bellows is in a partially compressed state as shown most clearly in FIGS. 4 and 6. External pad 12 is immobilized against labia majora 30 and functions as a base against which the expansive force of the bellows is applied in a downward direction. The upward force exerted by cup 11 against the periurethral surfaces is therefore relatively constant in magnitude and direction.

The bellows not only exerts a constant gentle upward force on the cup, to maintain the cup in the position illustrated, but also is capable of twisting, bending, and deflecting to accommodate changes in position of external pad 12 and internal cup 11 resulting from the dynamics of body movement. FIG. 5 illustrates what is believed to be a typical condition where, because of wearer movement, the cup 11 and pad 12 have become laterally disposed but, nevertheless, the expansive force exerted by bellows 13 coupled with the substantial contact surfaces between the form-retentive but compressible cup and the periurethral surfaces still maintain the cup in sealing contact with the wearer.

FIG. 7 illustrates a sizing instrument 40 that may be conveniently used for establishing the bellows length required for properly fitting a wearer with urinary collection device 10. Periurethral cup 111 is of substantially the same size and shape as cup 11 previously described, the essential difference being that cup 111 is secured or formed at the upper end of a stiff calibrated tube 41 rather than extending from a resilient bellows 13. The external pad 112 may be similar to previously described pad 12, being formed of a resilient elastomeric material (Dow Corning Q7-4840 has been found particularly effective) and having essentially the same dimensions. The primary difference is that instead of being secured to bellows 13 and flexible tube 14, external pad 112 may be provided with a sleeve 42 that slidably receives rigid calibrated tube 41. The external pad 112 may therefore be slid along the length of tube 41, and its position established by reference to calibration lines 43 and numerical indicia 44.

The sizing instrument 40 may be disposable and is used by a doctor or other medically-trained personnel by inserting periurethral cup 111 into the position assumed by cup 11 in FIG. 4, and then sliding the external pad 112 axially along the indexed tube 41 until the pad bears against the labia majora 30 in the same manner shown in FIG. 4 for pad 12. If inspection is deemed necessary or desirable to establish that the periurethral cup 111 is properly seated against the periurethral floor and vaginal introitus, or if inspection is required for any other reason, the doctor may insert the stem of a conventional endoscope through the passage 45 of tube 41, so that the objective of the endoscope extends into the open cup 112. Once it is determined that both the periurethral cup 111 and the external pad 112 are properly positioned, the sizing instrument is removed and the determination of bellows length for the collection device 10 to be used by the patient is made from scale 43–44.

The following example details the preparation of a soft, compressible material, and the construction of a periurethral cup formed of such material, found to be particularly effective for use in practicing the invention: Ten parts by weight of a first component and 7 parts by weight of a second component of a two-part silicone rubber addition polymerization system, type Q7-4840 from Dow Corning, Midland, Mich., were mixed with 1.7 parts by weight of type 360 Dow Corning silicone fluid having a viscosity of about 350 centipoises, and then degassed and injected into molds for the periurethral cup 11, the external pad 12, and bellows 13. Curing was achieved by heating to a temperature of 200°-400° F. for an interval of up to about 6 minutes. The silicone rubber of the final parts was homogeneous, smooth and clear (semi-transparent), with a durometer of approximately 10 Shore A.

The parts may also be fabricated from an elastomeric foam as follows: Four parts by weight of a slicone foam base, type Q7-4290 from Dow Corning, Midland, Mich., having a viscosity within the range of 1,000 to 6,000 centipoises, and 2.5 parts by weight of Silastic 382 elastomer from the same source, having a viscosity within the range of 35,000 to 65,000 cp, were mixed thoroughly and 0.045 part of a silicone foam catalyst, type Q7-4290, was then added and mixed thoroughly for approximately 30 seconds. The mixture was allowed to degas for approximately 30 seconds and then stirred vigorously. The degasing and stirring procedures were repeated twice, and the mixture was then immediately poured into molds for the periurethral cup 11 and the external pad 12. The cup and pad were removed from their respective mold cavities from a curing interval of approximately 12 minutes. To facilitate removal, the cavities of the molds were pre-coated with a suitable mold release agent (HEM 41220). The small cell size of the foam parts were promoted by the degasing procedures and the vigorous stirring action. The final parts had smooth, substantially non-porous outer surfaces or skins and a durometer of approximately 10 Shore A.

The embodiment depicted in FIGS. 8-16 is essentially the same as the embodiment of FIGS. 1-6 except for air porting and gas venting means. The device includes an external pad 212 for contacting the labia majora of the wearer, a periurethral cup 211 having upper and lower openings 217 and 218, respectively, and a tubular elastic bellows 213 extending between the lower opening of the cup and the opening of the external pad for urging the cup into engagement with the periurethral floor and vaginal introitus when the pad is held against the labia majora. The cup has an integral side wall 219 composed of front, rear, and lateral wall portions 219a, 219b, and 219c, respectively. In the region bordering top opening 217, each of those wall portions has smoothly rounded surfaces and has a substantial thickness within the range of about 3 to 15 millimeters. The rear wall portion 219b curves upwardly beyond the upper limits of the front and lateral wall portions to define the resilient, vaginally-insertable, urine-deflecting extension or protuberance 220. All of the characteristics, compositions, dimensions, and functions of the cup, bellows, and pad of this embodiment are essentially the same as those described in connection with the first embodiment of FIGS. 1-6.

Whether bellows 213 and cup 211 are formed separately (and then joined by adhesive or any other suitable means, as shown and previously described) or integrally, the upper end of the bellows 213 communicates directly with the periurethral cup 211 at lower opening 218. The lower end of the bellows is connected to the upper end of a flexible conduit or tube 214 by an extension 225 of that conduit. As shown most clearly in FIGS. 8 and 10, the interfacial conduit extension 225 has a wall 225a that flares upwardly and outwardly to match the larger diameter of the bellows. However, one portion 225b of that wall extends generally horizontally, that is, in a plane normal to the axis of the bellows in an undeformed state. One or more air entry ports 250 extend vertically (i.e., axially) through wall portion 225b; in the form shown, a pair of such ports are provided, each having an arcuate configuration when viewed in transverse section or plan (FIG. 11). Valve means 251, which may take the form of an umbrella valve having a conical canopy portion 252 and stem portion 253 is positioned to allow entry of ambient air while at the same time blocking the escape of fluids (gases and liquids) from the bellows 213 and upper end of the conduit 214. As shown most clearly in FIGS. 12-14, the elongated stem 253 of the valve member 251 is adapted to extend downwardly through an opening 254 in wall portion 225b, such opening being centered between arcuate ports 250. An intermediate enlargement 253a of the stem serves to limit upward movement of the stem with respect to wall portion 225b; downward movement is prevented by an upper enlargement 253b of the stem shrouded by the conical canopy portion 252.

The umbrella valve member 251 is composed of a soft, easily-deformable and readily-recoverable elastic material such as, for example, silicone rubber. FIG. 13 depicts the valve member in an untensioned or undeformed state, but it will be noted from FIG. 14 that when the valve member is secured to apertured wall 225b of the interfacial conduit extension 225 the valve member is in a pre-tensioned or pre-loaded condition with canopy portion 252 having a distinctive downward and outward curvature and with the peripheral edge of the canopy portion held in normal sealing engagement with the upper surface of wall 225b. Because of its deformability, and notwithstanding the pre-tensioning, the canopy portion 252 of the valve member is capable of flexing upwardly to allow entry of air into the system when even a small pressure differential (for example, 0.5 inches $H_2O$) exists. Such upward flexure is indicated in broken lines in FIG. 12. On the other hand, should the pressure within the system be equal to or exceed ambient pressure, the highly flexible canopy 252 will effectively seal against the upper surface of wall portion 225b and will block exit of fluids, at least within the range of pressure differentials encountered in normal use of the device. As shown in FIG. 10, the external pad 212 has an inlet passage 255 communicating with opening 250 in wall portion 225b. Passage 255 extends upwardly through the wall of the pad from an entrance 256 at the pad's lower end.

The purpose of ports 250 and valve members 251 is to insure that the superior sealing action of the periurethral cup against the periurethral floor and vaginal introitus will not interfere with proper flow of urine through conduit 214 to pouch or collection device 257. If it were not for the inlet ports, a column of liquid flowing downwardly through conduit 214 would generate a relative negative pressure that might even be sufficient to collapse bellows 213 and/or conduit 214, interfere with the fit of periurethral cup 211, and possibly result in leakage or wearer discomfort. Since ports 250 and one-way valve 251 permit the entry of air at the upper end of the conduit, pressure is equalized and such problems are thereby avoided.

While the umbrella valve construction shown in the drawings has been found highly effective, other types of air-inletting valves might be used. Furthermore, where an umbrella valve is utilized, it may or may not be used in conjunction with deflector means 253. The purpose of the deflector is simply to prevent the possibility that leakage might occur should canopy 252 of the valve member 251 be impacted by a stream of urine flowing rapidly through the bellows 213 and entering conduit 214. If the possibilities of leakage caused by urine impinging upon and deforming the valve member are considered so slight as to be negligible or inconsequential then deflector 258 may be eliminated.

As shown in FIGS. 12 and 14–16, the deflector 258 takes the form of a plate 259 having a pair of spaced downwardly-extending legs 260. The cover plate 259 extends over the canopy 252 of valve member 251 and is held in place by upstanding spindles or lugs 261 that are formed integrally with interfacial conduit extension 225 and received within channels or holes 262 formed in the legs 260 of the deflector. The deflector may be frictionally held in place by the lugs and, as shown, the free ends of the lugs may be flattened and thereby laterally enlarged to lock the deflector in operative position. Alternatively, the parts may be permanently bonded or fused together by any suitable means.

To prevent air which enters the system through ports 250 from inflating pouch 257, a wall 257a of the pouch is provided at its upper end with air venting means 270. Any suitable means for venting air from the upper end of the pouch while at the same time blocking the outflow of liquid may be used. In the embodiment illustrated, the venting means takes the form of perforations 271 formed in wall 257a with the area of such perforations backed by a thermoplastic microporous strip 272 capable of allowing gases to escape from the pouch while at the same time blocking the passage of urine. The strip or patch 272 is perimetrically sealed to the wall of the pouch by heat sealing 273 or by any other suitable sealing means. While various types of hydrophobic microporous materials may be used for fabrication of the vent or filter patch 272, effective results have been achieved using 3-micron filter stock marketed under the designation "Versapor" by Gelman Corporation, Ann Arbor, Mich.

The lower or distal end of flexible conduit 214 is shown to be connected to pouch 257 by a detachable coupling 280 of the type shown and described in co-owned U.S. Pat. No. 4,280,498. Reference may also be had to copending application Ser. No. 273,363, filed June 15, 1981, for a manner of forming an effective liquid-tight seal between the conduit and the pouch while, at the same time, allowing limited pivotal action between the conduit and pouch. Since any of a variety of couplings and connections between the conduit and the pouch might be provided, all within the knowledge of someone familiar with urine collection systems, a discussion of such structures in further detail is believed unnecessary herein.

While in the foregoing we have disclosed embodiments of the invention in considerable detail for purposes of illustration, it will be understood by those skilled in the art that many of these details may be varied without departing from the spirit and scope of the invention.

We claim:

1. A female urinary incontinence device comprising an external pad of flexible, resilient material for externally contacting the libia majora of a wearer, said pad having an opening therethrough; a periurethral cup molded of soft compressible material and having an upper opening defined by smoothly-rounded contact surfaces adapted to engage the periurethral floor and vaginal intrioitus of a wearer; said compressible material having a durometer within the range of about 1 to 30 on the Shore A scale; said cup also having a lower opening; compressible tubular elastic bellows means extending between said lower opening of said cup and said opening of said pad for urging said cup into engagement with said periurethral floor and vaginal intrioitus when said pad is held against the labia majora and said bellows means is in a state of partial compression; conduit means extending into said opening of said pad and joined to, and in fluid communication with, the lower end of said bellows; said conduit means including a wall having a vent port extending therethrough with said port located immediately adjacent said external pad and the lower end of said bellows; and one-way valve means at said port for allowing air to enter said bellows and cup, as liquid travels away from said bellows through said conduit means, while at the same time preventing the escape of liquid through said port.

2. The device of claim 1 in which a urine collection pouch is connected to said conduit means; said pouch being provided with a wall having a gas vent extending therethrough; and means for preventing the escape of liquids from said pouch through said vent.

3. The device of claim 1 in which retaining means are provided for holding said pad against the labia majora of a wearer to maintain said bellows means in said state of partial compression.

4. The device of claim 1 in which said cup includes front, rear, and side wall portions having upper surfaces merging smoothly with each other and being of rounded cross-sectional contour to provide wide gently-curved contact surfaces for sealingly engaging the periurethral floor and vaginal introitus of a wearer.

5. The device of claim 4 in which said rear wall portion extends a substantial distance upwardly beyond said front and side wall portions to define a resilient vaginally-insertable urine-deflecting protuberance.

6. The device of claim 5 in which said urine-deflecting protuberance is capable of flexing towards and away from said upper opening without causing buckling or kinking of the contact surfaces of said cup at the merger of said side and rear wall portions because of the compressibility and substantial wall thickness of said cup.

7. The device of claims 4 or 5 in which said wall portions of said periurethral cup have thicknesses adjacent said upper opening within the range of about 3 to 15 millimeters.

8. The device of claim 7 in which said material of said cup has a durometer within the range of about 5 to 20 on the Shore A scale.

9. The device of claim 8 in which said material of said cup has a durometer of approximately 10 on the Shore A scale.

10. The device of claim 1 in which said material of said cup is an elastomeric foam.

11. A female urinary incontinence device comprising an external pad of flexible, resilient material having a concave upper surface for externally contacting the labia majora and having an opening extending therethrough; a periurethral cup molded of soft, compressible material having front, rear, and side wall portions with upper surfaces merging smoothly with each other and being of rounded cross-sectional contour to provide wide, curved contact surfaces for engaging the periurethral floor and vaginal introitus; said rear wall portion extending upwardly beyond said front and side wall portions to define a resilient, vaginally-insertable, urine deflecting protuberance; said compressible material of said periurethral cup having a durometer within the range of about 1 to 30 on the Shore A scale; said protuberance being capable of flexing towards and away from said upper opening without causing buckling and kinking of said contact surface of said cup at the merger of said side and rear wall portions; said cup also having a lower opening; compressible tubular elastic bellows means extending between said lower opening of said cup and said opening of said pad for urging said cup into engagement with the periurethral floor and vaginal introitus when said pad is supported against the labia majora and said bellows means is in a state of partial compression; conduit means extending into said opening of said pad and joined to, and in fluid communication with, the lower end of said bellows; said conduit means including a wall having a vent port extending therethrough with said port being located immediately adjacent said external pad and the lower end of said bellows; and one-way valve means connected to said wall at said port for allowing ambient air to enter said bellows and cup, as liquid travels away from said bellows through said conduit means, while at the same time preventing the escape of liquid through said port.

12. The device of claim 11 in which a urine collection pouch is connected to said conduit means; said pouch being provided with a wall having a gas vent extending therethrough; and means for blocking the escape of liquids from said pouch while allowing gases to pass through said vent.

13. The device of claim 11 or 12 in which said material of said cup has a durometer within the range of about 5 to 20 on the Shore A scale.

14. The device of claim 13 in which said material of said cup has a durometer of approximately 10 on the Shore A scale.

15. The device of claim 13 in which said material of said cup is silicone rubber.

16. The device of claim 13 in which said material of said cup is elastomeric foam.

17. The device of claim 16 in which said elastomeric foam of said cup has a substantially non-porous outer skin.

18. The device of claim 11 in which said wall portions of said periurethral cup have thicknesses within the range of about 3 to 15 millimeters.

* * * * *